United States Patent
Soliman et al.

(10) Patent No.: US 8,453,644 B2
(45) Date of Patent: Jun. 4, 2013

(54) SYSTEM AND METHOD FOR CIRCUIT COMPLIANCE COMPENSATED PRESSURE-REGULATED VOLUME CONTROL IN A PATIENT RESPIRATORY VENTILATOR

(75) Inventors: Ihab S. Soliman, Laguna Niguel, CA (US); Steven Duquette, Laguna Niguel, CA (US)

(73) Assignee: CareFusion 207, Inc., San Diego, CA (US)

( * ) Notice: Subject to any disclaimer, the term of this patent is extended or adjusted under 35 U.S.C. 154(b) by 96 days.

(21) Appl. No.: 13/039,963

(22) Filed: Mar. 3, 2011

(65) Prior Publication Data

US 2011/0214672 A1 Sep. 8, 2011

Related U.S. Application Data

(62) Division of application No. 11/270,787, filed on Nov. 9, 2005, now Pat. No. 7,918,223.

(51) Int. Cl.
*A61M 16/00* (2006.01)
(52) U.S. Cl.
USPC ............ 128/204.21; 128/204.18; 128/204.22; 128/204.23; 128/204.24; 128/204.25; 128/204.26
(58) Field of Classification Search
USPC .............................. 128/204.18, 204.21–204.26
See application file for complete search history.

(56) References Cited

U.S. PATENT DOCUMENTS

| | | | |
|---|---|---|---|
| 3,729,003 | A | 4/1973 | Hurschman |
| 3,834,381 | A | 9/1974 | Peterson |
| 3,923,056 | A | 12/1975 | Bingmann et al. |
| 4,448,192 | A | 5/1984 | Stawitcke et al. |
| 5,271,298 | A | 12/1993 | Gazel-Anthoine |
| 5,881,717 | A | 3/1999 | Isaza |
| 5,931,162 | A * | 8/1999 | Christian ............... 128/204.23 |
| 6,557,553 | B1 | 5/2003 | Borrello |
| 6,932,084 | B2 | 8/2005 | Estes et al. |
| 7,246,618 | B2 | 7/2007 | Habashi |
| 7,267,122 | B2 | 9/2007 | Hill |
| 7,484,508 | B2 | 2/2009 | Younes |

* cited by examiner

*Primary Examiner* — Clinton T Ostrup
(74) *Attorney, Agent, or Firm* — McDermott Will & Emery LLP (57) ABSTRACT

A system and a method for circuit compliance compensated pressure control in a patient respiratory ventilation system, having a pressure regulated feedback servo control loop, a pressure-regulated volume controller, and a patient volume observer. The patient volume observer is operative to estimate a patient volume, that is, the volume actually delivered to the patient by accounting for volume deviation or loss caused by patient circuit leakage and valve dynamics. Based on the difference between the estimated patient volume and a set tidal volume, the pressure-regulated volume controller is operative to generate and update a circuit compliance pressure compensation factor. The pressure regulated feedback servo control loop is operative to modulate the peak airway pressure based on the circuit compliance pressure compensation factor, so as to achieve the set tidal volume while maintaining a constant inspiratory time and a constant I:E ratio.

11 Claims, 6 Drawing Sheets

SYSTEM AND METHOD FOR CIRCUIT COMPLIANCE COMPENSATED PRESSURE-REGULATED VOLUME CONTROL IN A PATIENT RESPIRATORY VENTILATOR

CROSS-REFERENCE TO RELATED APPLICATIONS

This application is a divisional of claims the benefit of U.S. patent application Ser. No. 11/270,787, with filing date Nov. 9, 2005 now U.S. Pat. No. 7,918,223 assigned to the assignee of the present application.

STATEMENT RE: FEDERALLY SPONSORED RESEARCH/DEVELOPMENT

Not Applicable

BACKGROUND

The present invention relates in general to a system and a method for circuit compliance compensated pressure-regulated volume control in a patient respiratory ventilator, and more particularly, to a system and a method suitable for providing ventilation to patients at all sizes and ages by effectively and accurately estimating and compensating for the patient circuit compliance.

In order to deliver an accurate set tidal volume to a patient in a respiratory ventilation system, the patient circuit compliance has to be compensated. The compensation of patient circuit compliance is especially crucial for neonatal patients whose lung compliance can be as small as about one thirteenth of the circuit compliance. Without compensation for the circuit compliance, inaccurate volume delivery and inadequate flow will be delivered to the patient. Therefore, various designs and algorithms have been proposed to facilitate the patient circuit compliance compensation in the respiratory ventilation system. Currently, the setting or approaches in many of the circuit compliance compensation designs or algorithms cannot achieve precise volume delivery especially for neonatal patients without the risk of over delivering volume. Therefore, most of the ventilators available in the market do not allow for circuit compliance compensation designs applied to neonatal patients due to the stringent precision requirement on volume delivery. The burden of achieving accurate volume delivery is then left for the clinician.

Currently, algorithms that directly add an estimate of patient circuit volume to a set tidal volume are commonly used. An estimate of patient circuit volume is added to a set tidal volume by increasing the volume target, which ultimately increments the target peak airway pressure. The patient circuit volume is computed using the average peak airway pressure of previous mandatory breaths and an estimate of the patient circuit compliance, the patient circuit volume is thus continuously elevated breath after breath. Due to positive feedback of average peak airway pressure, when directly accounting for the circuit volume this algorithmic approach can establish a runaway (not converge) condition especially on neonatal patient sizes where the ratio of circuit compliance to patient (lung) compliance can be as high as 13:1. Moreover, this algorithm is not robust in cases where airway resistance is high due to effects such as gas compression which occurs as a result of positive feedback of peak airway pressure. Therefore, this algorithm is only effective on adults and some pediatrics patient sizes, and may not be responsive when changes in airway resistance and/lung compliance occur. A positive feedback approach to directly account for the circuit compliance/volume can thus have many adverse affects.

Therefore, there is a substantial need to develop a system and a method to provide circuit compliance compensated pressure regulated volume control in a patient respiratory ventilation system for the patients at all ages and sizes without causing any of the above adverse effects.

BRIEF SUMMARY

A system and a method for circuit compliance compensated pressure-regulated volume control in a patient respiratory ventilator clinically acceptable for patients at all sizes and ages are provided. The system and method as provided allow the patient to receive an accurate patient pressure while maintaining a constant ratio of inspiratory time versus expiratory time (I:E ratio) throughout volume delivery without causing gas trapping and auto PEEP. The existing onboard sensors are used for modulate the target airway pressure, so as to provide the set tidal volume to the patient. The operation of the system and the method are designed based on the governing physics of the patient/ventilator system, and the leakage of the patient circuit and actuator response & dynamics are taken into account during volume delivery. Therefore, the system and method are robust against changes in airway resistance and patient compliance.

A system for circuit compliance compensated pressure-regulated volume control in a patient respiratory ventilation system, having a pressure regulated feedback servo control loop, a pressure-regulated volume controller, and a patient volume observer. The patient volume observer is operative to estimate a patient volume, that is, the volume actually delivered to the patient by accounting volume deviation or loss caused by patient circuit leakage or actuator dynamics. Based on the difference between the estimated patient volume and a set tidal volume, the pressure-regulated volume controller is operative to generate and update a circuit compliance pressure compensation factor. The pressure regulated feedback servo control loop is operative to regulate the peak airway pressure of the patient based on the circuit compliance pressure compensation factor, so as to achieve the set tidal volume delivery while maintaining a constant inspiratory time and a constant I:E ratio.

In one embodiment, a method for circuit compliance compensated pressure-regulated volume control is provided. The method includes generating a circuit compliance pressure compensation factor based on a set tidal volume and an actual volume delivered to the patient. The actual volume delivered to the patient can be estimated by measurements from existing flow sensors and pressure transducer or measured directly from a flow sensor at the patient connection. The circuit compliance pressure compensation factor is updated by a dynamic gain which varies according to a ratio of volume distributed to the patient circuit and the volume flowing to the patient. The dynamically updated circuit compliance pressure compensation factor is then used to regulate a peak airway pressure. Based on the regulated peak airway pressure, the ventilator is operative to supply an appropriate net volume allowing the actual volume delivered to the patient to approach the set tidal volume within a few breaths.

A ventilation system that incorporating the above the system for circuit compliance compensated pressure regulated volume control is also provided. The ventilation system includes a ventilator for supplying inspiratory gas to the patient and re-circulating the expiratory gas exhaled from the patient and a patient circuit, preferably a Y-circuit, for providing the flow communication between the ventilator and the patient. Sensors and transducers are provided to measure the inspiratory flow, expiratory flow, patient flow, circuit pressure, and PEEP. By measurements of the above parameters, a circuit compliance compensation pressure factor can be generated and updated for regulating a peak airway pressure. The updated peak airway pressure is input to a servo control subsystem to control operation of the ventilator, such that the ventilator can deliver a net volume allowing the desired or predetermined set tidal volume to be delivered to the patient without prolonging the inspiratory time, so as to maintain a constant I:E ratio.

BRIEF DESCRIPTION OF THE DRAWINGS

These and other features and advantages of the various embodiments disclosed herein will be better understood with respect to the following description and drawings, in which like numbers refer to like parts throughout, and in which.

DETAILED DESCRIPTION

Figure 1:
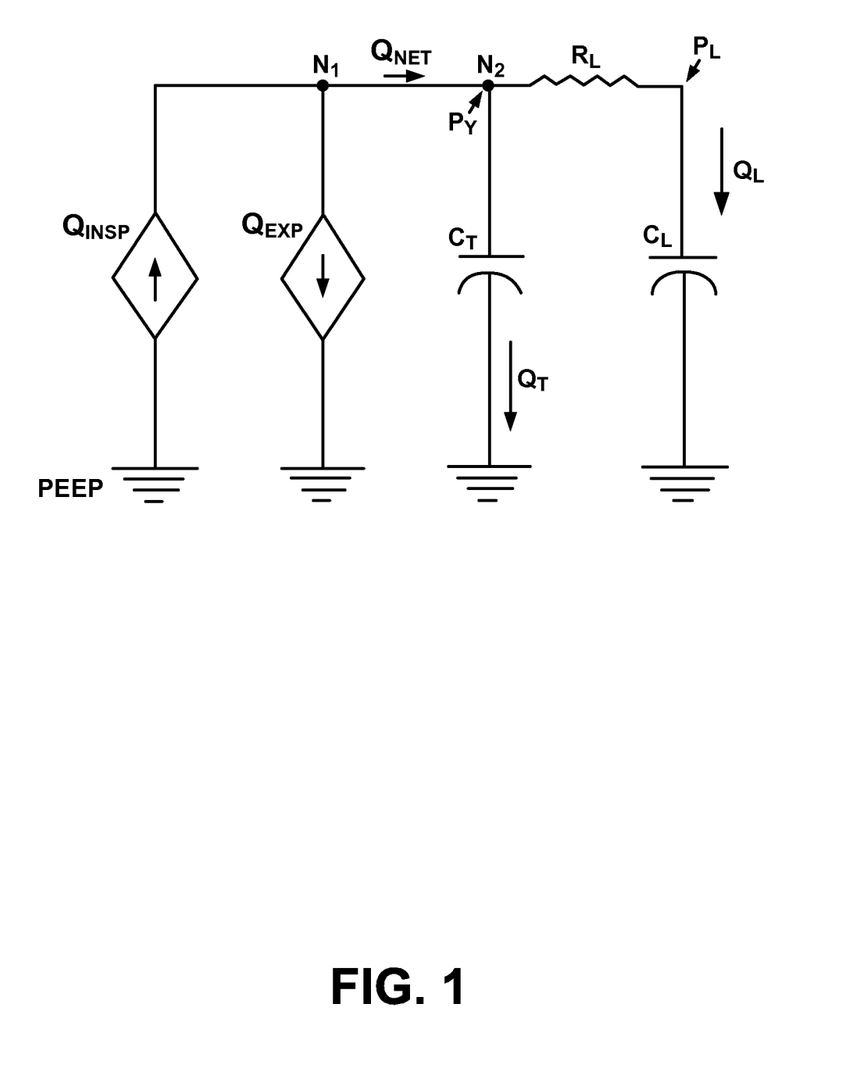
FIG. 1 illustrates a respiratory circuit diagram of a patient who is receiving machine ventilation.

In an electric circuit, the electric current I flows from a high potential level to a low potential level. When the electric current flows through a passive circuit element such as a resistor, an inductor, a capacitor, or a load, a voltage drop $\Delta V$ is created across such element. When electric circuit comprises two or more of the similar circuit elements connected to each other in parallel, the total electric current is split into two smaller currents distributed flowing through the respective elements. The magnitude of the distributed currents depends on the characteristic values, such as the resistance, the conductance and the capacitance of the elements. In a patient respiratory circuit, the gas flow Q circulates from a high pressure level to a low pressure level in a way similar to the electric current I in the electric circuit; and the gas flow I flowing through an airway resistance causes a pressure drop $\Delta P$ similar to the voltage drop $\Delta V$. FIG. 1 illustrates a circuit diagram of a patient respiratory circuit. As shown, the patient respiratory circuit comprises a patient circuit for circulating gas between a ventilator and a patient. The ventilator is operative to provide an inspiratory gas flow $Q_{INSP}$ to the patient and receive an expiratory gas flow $Q_{EXP}$ exhaled from the patient through the patient circuit. Ideally, 100% of the net flow $Q_{NET}$ delivered from the ventilator, that is, the flow differential between the inspiratory flow $Q_{INSP}$ and the expiratory flow $Q_{EXP}$, is to be delivered to the patient, such that the set tidal volume can be delivered to the patient. However, in real practice, the volume loss within the patient circuit is inevitable due to the distensibility at least partially attributed to the circuit compliance $C_T$ thereof. As shown, the circuit compliance $C_T$ that behaves similarly to a capacitor in an electric current is in parallel flow communication with the lung compliance $C_L$ in the patient respiratory circuit.

By measuring the inspiratory flow $Q_{INSP}$ and the expiratory flow $Q_{EXP}$, the machine delivered net volume $V_{NET}$ can be computed by integrating by the net gas $Q_{NET}$, that is, the flow differential between the inspiratory flow $Q_{INSP}$ and the expiratory flow $Q_{EXP}$. Without the circuit compliance compensation, the machine delivered net volume $V_{NET}$ is equivalent to the set tidal volume delivered by the ventilator. However, as a portion of the net flow $Q_{NET}$ is offset by the circuit compliance $C_T$, the volume actually delivered to the patient's lung is smaller than the set tidal volume. That is, the patient cannot receive the set tidal volume as desired. As the circuit compliance $C_T$ is defined as a ratio of the volume offset by the patient circuit to the pressure across the patient circuit, the volume offset by the circuit compliance is thus proportional to the circuit compliance $C_T$. Therefore, when the circuit compliance $C_T$ is much larger than the lung compliance $C_L$, a majority part of the net flow $Q_{NET}$ will be distributed to the patient circuit instead of being supplied to the patient's lung.

In the embodiment as shown in FIG. 1, the ground level that the patient circuit connects to is set at the positive end expiratory pressure (PEEP). Therefore, the pressure drop across the patient circuit is the pressure differential $\Delta P$ between the measured pressure $P_Y$ and PEEP. Typically, an airway resistance $R_L$ exists in the patient's airway, such that the pressure applied to the patient's lung will be offset by a factor of $Q_L^2 R_L$. The pressure at the patient circuit $P_Y$ and the lung pressure $P_L$ can thus be expressed by the following equation:

$$P_Y = P_L + Q_L^2 R_L \tag{1}$$

By definition, the circuit compliance $C_T$ and the lung compliance $C_L$ can be expressed as:

$$C_L = \frac{V_{TID}}{P_L - PEEP}; \tag{2}$$

and $$C_R = \frac{V_{CC}}{P_Y - PEEP}, \tag{3}$$

where $V_{TID}$ is equivalent to $V_L$, which is the actual gas volume delivered to the lung of the patient, and $V_{CC}$ is the gas volume offset by the circuit compliance. The gas volumes $V_{TID}$ and $V_{cc}$ can be derived by integrating the gas flow $Q_T$ and $Q_L$ flowing through the patient circuit and the patient's lung L. Therefore, the sum of the gas volumes $V_{cc}$ and $V_L$ is equal to the net gas volume $V_{NET}$ as expressed by Equation (4), which can be integrated from the net gas flow $Q_{NET}$.

$$V_{NET} = V_{cc} + V_{TID} \tag{4}$$

From Equations (3) and (4), an estimate of patient volume can be expressed as:

$$V_{TID} = V_{NET} - V_{CC} = V_{NET} - C_T(P_Y - PEEP) \tag{5}$$

From Equations (1) and (2), $$P_y - PEEP = \frac{V_{TID}}{C_L} + Q_L^2 R_L. \tag{6}$$

From Equations (5) and (6), an estimate of the net volume that the ventilator needs to deliver is:

$$V_{NET} = V_{TID} + C_T(P_Y - PEEP) \quad (7)$$

or $$V_{NET} = V_{TID} + C_T\left(\frac{V_{TID}}{C_L} + Q_L^2 \cdot R_L\right);$$

and therefore, $$V_{NET} = \left(1 + \frac{C_T}{C_L}\right)V_{TID} + C_T \cdot Q_L^2 \cdot R_L.$$

From Equation (7), the machine delivered volume $V_{NET}$ can be computed if the lung compliance $C_L$, the circuit compliance $C_T$, the airway resistance $R_L$, the desired patient flow $Q_L$, and the desired patient flow $V_{TID}$ are known. It will be appreciated that, as the volume parameters in Equation (7) are integrations of the corresponding gas flows, the pressure parameter $P_Y$ typically indicates the peak pressure at the patient circuit.

In Equation (7), since the lung compliance $C_L$ and the airway resistance $R_L$ can vary with time or condition, it would be very difficult to accurately determine the appropriate machine delivered volume as desired on a real-time basis. Therefore, as provided in this embodiment, the system and method for circuit compliance compensated pressure control estimate the patient volume and the patient circuit volume using the existing sensors in the ventilator. For example, the actual inspiratory gas flow $Q_{INSP}$ and the expiratory gas flow $Q_{EXP}$ are measured by the existing sensors of the ventilation machine used by the patient, and the net machine delivered flow $Q_{NET}$ can be derived from the difference thereof. Alternatively, the machine delivered net flow $Q_{NET}$ can be obtained from direct measurement by the sensor installed at the patient circuit. In such manner, various volume variables can be obtained based on the true inhalation and exhalation of the patient, and the set peak airway pressure can be regulated based on the volume variables.

By definition, the positive end expiratory pressure PEEP is the pressure $P_Y$ measured at the end of the expiratory phase. Therefore, before the patient is receiving the machine ventilation, the ground pressure level of the patient circuit is zero or other preset values. The circuit compliance $C_T$ can be predetermined by providing known volumes to the patient circuit and measuring the responsive circuit pressure at each specific volume as supplied. The circuit compliance $C_T$ for a specific patient circuit can thus be expressed by an empirical relationship between the circuit volume $V_{CC}$ and the circuit pressure $\Delta P_Y$ (=$P_Y$). When the patient circuit is applied to circulate gas between the ventilator and the patient to construct the patient respiratory circuit as shown in FIG. 1, one can then derive the circuit volume $V_{CC}$ from the empirical relationship by measuring the circuit pressure $\Delta P_Y$ (=$P_Y$-PEEP). In this embodiment, the pressure $P_Y$ is defined as the pressure measured at the expiratory limb of the patient circuit during the inspiratory phase, that is, $P_Y=P_{EXP}$ during I-phase; or $P_Y$ is the average pressure between $P_{EXP}$ and the pressure measured at the inspiratory limb of the patient circuit during the expiratory phase $P_{INSP}$, that is, $P_Y=(P_{INSP}+P_{EXP})/2$ during E-phase.

Figure 2:
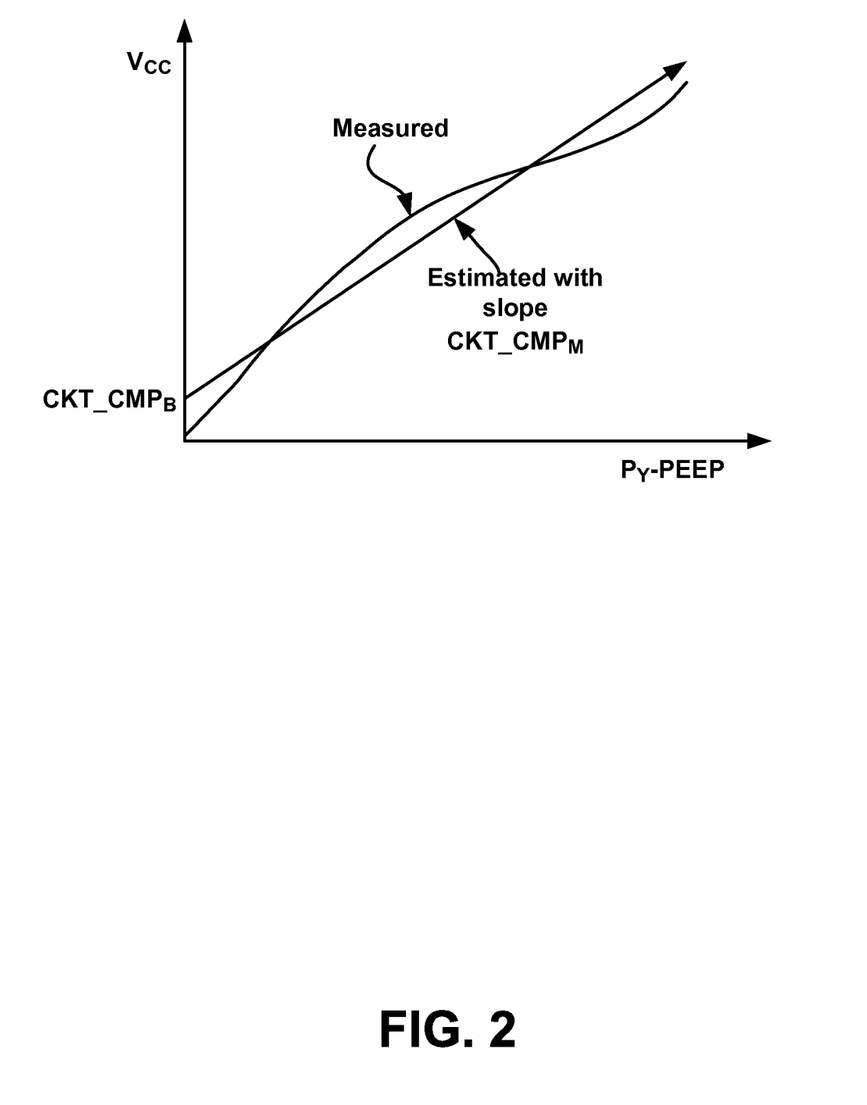
FIG. 2 shows a graph of circuit compliance obtained from empirical data and an estimated circuit compliance approximated from the empirical data.

FIG. 2 shows the relationship between the circuit volume $V_{CC}$ and the pressure differential $\Delta P_Y$ obtained from empirical data. As shown, the empirical data show a nearly linear relationship between the circuit volume $V_{CC}$ and the differential circuit pressure $\Delta P_Y$. Therefore, a linear line with a slope $CKT\_CMP_{SLP}$ that reflects the circuit compliance $C_T$ can be drawn from the graph, and the circuit volume $V_{CC}$ can be presented by the equation as:

$$V_{CC}=CKT\_CMP_{SLP} \cdot (P_Y-PEEP)+CKT\_CMP_{INT} \quad (8),$$

where $CKT\_CMP_{INT}$ is the intercept with the $V_{CC}$ axis. It will be appreciated that, depending on specific setup parameters and conditions of the patient, the relationship between the circuit $V_{CC}$ and the circuit pressure $\Delta P_Y$ may vary from Equation (8). For example, a nonlinear behavior may be observed from the empirical data. Further, a lookup table listing the circuit volume for each responsive circuit pressure can also be used for one to estimate the circuit volume $V_{CC}$.

When the circuit volume of the patient circuit is obtained, the tidal volume actually delivered to the patient can be estimated from Equation (4), that is, $$V_{TID}=V_{NET}-V_{CC} \quad (9)$$

As mentioned above, the net volume delivered by the machine $V_{NET}$ can be derived by integrating the net flow delivered by the machine $Q_{NET}$, that is, the difference between the inspiratory and expiratory gas flows $Q_{INSP}$ and $Q_{EXP}$. That is, $$V_{NET}=\int_{Start\ of\ I\text{-}phase}^{Q_{NET}Crosses\ 0}[(Q_{INSP})-Q_{EXP})dt \quad (10)$$

In this embodiment, the circuit volume $V_{CC}$ will not be updated until the differential gas flow, that is, the net gas flow $Q_{NET}$ (=$Q_{INSP}-Q_{EXP}$) crosses zero; and therefore, the calculation or computation of the net machine delivered volume $V_{NET}$ is integrated over the differential gas flow $Q_{NET}$ from the start of the inspiratory phase to the time when the net flow $Q_{NET}$ crosses 0. In the case that the net flow $Q_{NET}$ crosses 0 before the inspiratory phase is complete, the circuit volume $V_{CC}$ and the tidal volume $V_{TID}$ are estimated.

Figure 3:
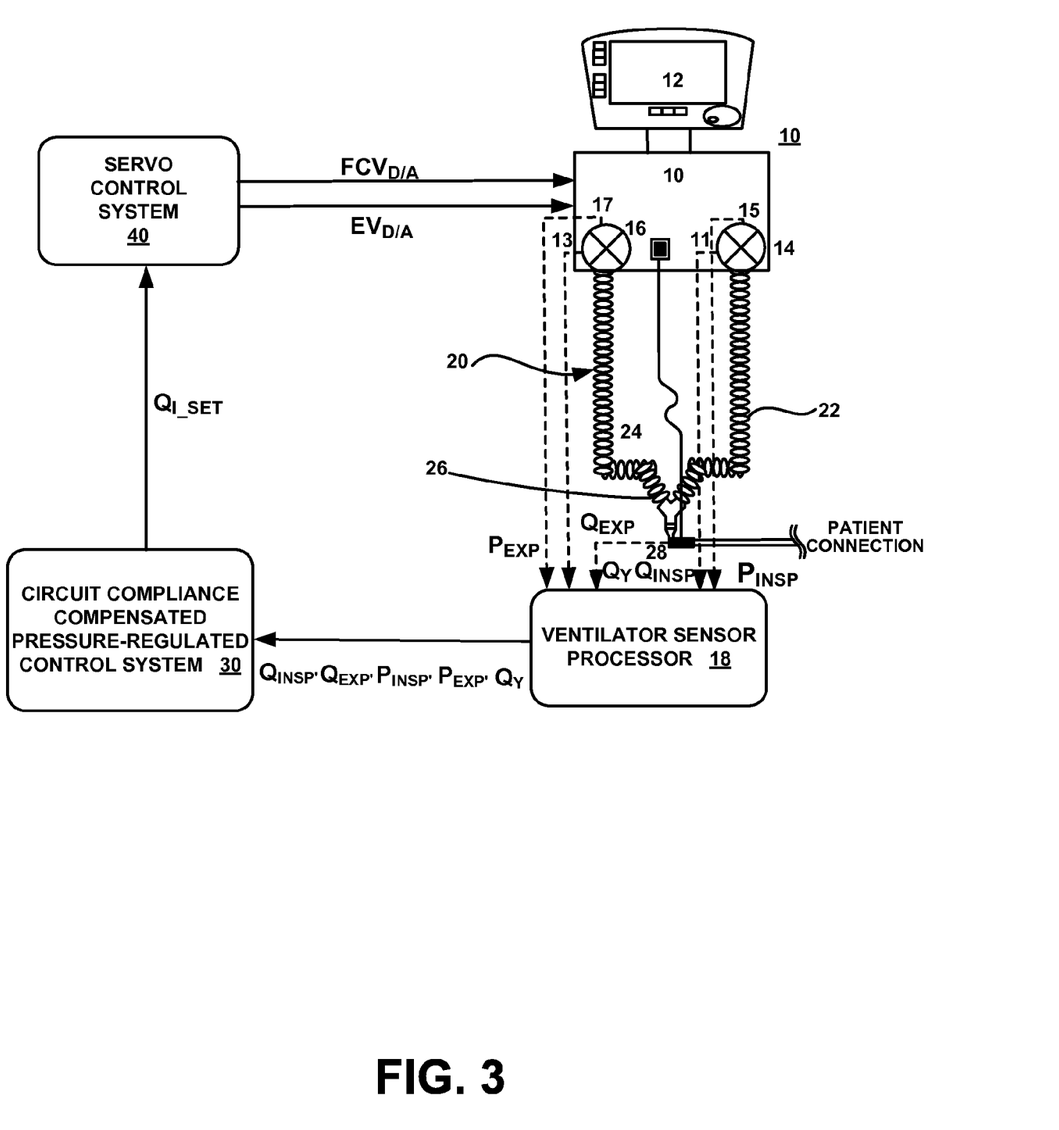
FIG. 3 illustrates a block diagram showing a ventilation system that incorporates a system for circuit compliance compensated pressure regulated volume control.

FIG. 3 illustrates a patient ventilation circuit or system incorporating the system for circuit compliance compensated pressure-regulated volume control discussed above. As shown in FIG. 3, the ventilation system includes a ventilator 10, a patient circuit 20 for circulating the inspiratory gas and the expiratory gas between the ventilator 10 and a patient, the system for circuit compliance compensated pressure-regulated volume control 30, and a servo control subsystem 40 for controlling operations of the ventilator 10. The ventilator 10 typically includes a user interface such as a monitor 12 for displaying various conditions and parameters of the patient and the ventilation system, and an input device (not shown) allowing the operator or user to input the required settings and parameters. The input device may include switches, buttons or any adjusting devices built on the front panel of the monitor or other devices including keyboard, mouse or remote controls operative to provide data or information input by the user or operator to a processor (not shown) of the ventilator 10. Alternatively, the monitor 12 may be in the form of a touch screen in which both the display and input device are integrated. Based on the input data or information, the processor is operative to control the ventilator 10 for performing the desired operations. The ventilator 10 further includes an inspiratory port 14 and an expiratory port 16 through which the inspiratory gas and the expiratory gas are supplied to and received from the patient through the patient circuit. An inhalation flow control valve or orifice is typically installed at the inspiratory port 14 for controlling the inspiratory flow $Q_{INSP}$, and an exhalation valve is preferably installed at the expiratory port for controlling the open/close condition of the expiratory port 16. In this embodiment, inspiratory and expiratory flow sensors 11 and 13 are installed at the inspiratory and expiratory ports 14 and 16 for measuring the inspiratory $Q_{INSP}$ and expiratory flow $Q_{EXP}$, respectively. In addition, an inspiratory pressure transducer 15 and an expiratory pressure transducer 17 may also be installed to measure the inspiratory and expiratory pressure $P_{INSP}$ and $P_{EXP}$, respectively.

As shown, the patient circuit 20, such as a Y circuit, is used to connect the ventilator 10 to the patient, so as to construct the respiratory circuit for circulating gas between the ventilator 10 and the patient. The Y circuit 20 includes an inspiratory limb 22 with one end connected to the inspiratory port 14 and an expiratory limb 24 with one end connected to the expiratory port 16 of the ventilator 10. The other ends of the inspiratory limb 22 and the expiratory limb 24 merge with each other at one end of a patient piece 26, of which the other end is applied to the patient. Other accessories or component devices such as filters may also be installed in various parts of the Y circuit 20. For example, a flow sensor 28 is preferably installed at the patient piece 26 to directly measure the patient flow $Q_Y$ delivered to the patient. It will be appreciated that the inspiratory and expiratory flow sensors 11 and 13 may also be installed on the inspiratory limb 22 and the expiratory limb 24, respectively. Preferably, the measurable process variables, including the inspiratory flow $Q_{INSP}$, the expiratory flow $Q_{EXP}$, the inspiratory pressure $P_{INSP}$, the expiratory pressure $P_{EXP}$, and PEEP are measured according to a predetermined sampling rate. For example, in one embodiment, these process variables are sampled every 2 msec. The ventilator 10 may further comprises a sensor processor 18 operative to process the measured process variables or parameters, including $Q_{INSP}$, $Q_{EXP}$, $P_{INSP}$, $P_{EXP}$ and other sensor readings such as $Q_Y$ before outputting them to the circuit compliance compensated pressure regulated volume control system 30. The sensor processor 18 may be configured as an individual sensor in communication with the sensors 11, 13, 15, 17 and 28 and the circuit compliance compensated pressure-regulated volume control system 30. Alternatively, the sensor processor 18 may be integrated into the above-mentioned processor of the ventilator 10 that control the operations of the ventilator 10.

Figure 4:
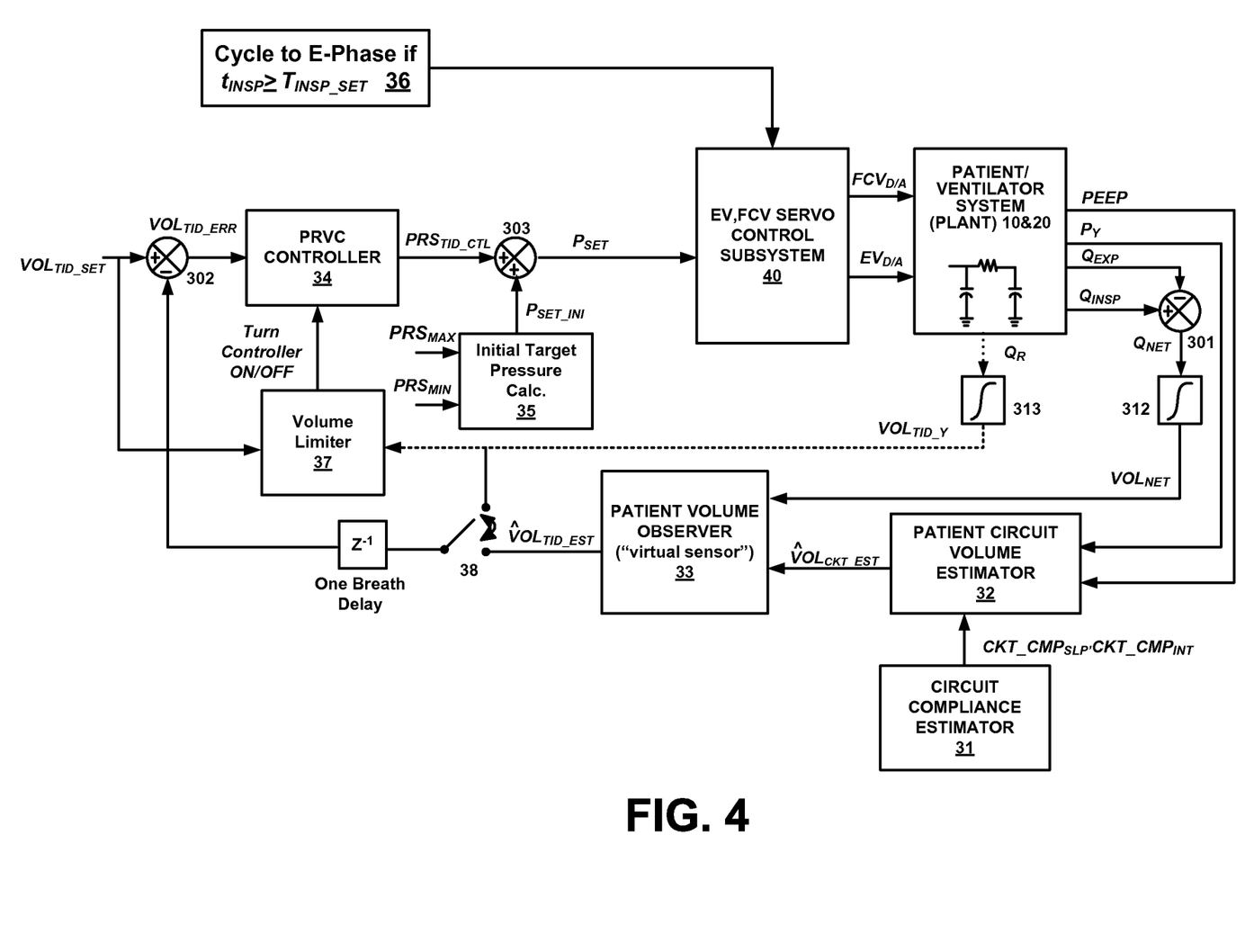
FIG. 4 shows a block diagram of the system for circuit compliance compensated pressure regulated volume control.

Referring to FIGS. 3 and 4, the system for circuit compliance compensated pressure regulated volume control 30 includes a circuit compliance estimator 31, a patient circuit volume estimator 32, a patient volume observer 33, a pressure-regulated volume controller 34, and an initial target pressure calculator 35. As discussed above, the circuit compliance $C_T$ of the patient circuit 20 can be estimated by measuring the pressure differential $\Delta P_Y$ various circuit volumes $V_{CC}$. In this embodiment, the circuit compliance estimator 31 is operative to provide a relationship between the circuit volume $V_{CC}$ and the pressure differential $\Delta P_Y$ based on empirical data. The relationship may be in the form of a mathematical equation of $V_{CC}$ and $\Delta P_Y$ a lookup table reflecting the corresponding circuit volumes $V_{CC}$ for a specific circuit pressure $\Delta P_Y$. When the empirical data show a linear relationship as expressed by Equation (8), the slope $CKT\_CMP_{SLP}$ and the intercept $CKT\_CMP_{INT}$ are estimated by the circuit compliance estimator. The slope $CKT\_CMP_{SLP}$ and the intercept $CKT\_CMP_{INT}$ of the circuit compliance estimator 31 are then output to the patient circuit volume estimator 32. The circuit volume estimator 32 is also connected to the ventilator 10 for receiving the Y circuit pressure $P_Y$ and the PEEP measured by the pressure transducers 17 (or 15 and 17), such that the pressure differential $\Delta P_Y$ can be computed. Based on $\Delta P_Y$, the slope $CKT\_CMP_{SLP}$ and the intercept $CKT\_CMP_{INP}$, the patient circuit volume $V_{CC}$ can be estimated by Equation (8) and denoted as $VOL_{CKT_{EST}}$ output to the patient volume observer 33.

The patient volume observer 33 is operative to receive the measured net machine delivered volume $VOL_{NET}$, that is, the machine delivered net volume derived by integrating the net flow $Q_{NET}$, and the estimated circuit volume $VOL_{CKT_{EST}}$ estimated by the circuit volume estimator 32. By subtracting the estimated circuit volume $VOL_{CKT_{EST}}$ from the measured machine delivered net volume $VOL_{NET}$ derived by integrating the net flow $Q_{NET}$, the true volume $VOL_{TID}$ delivered to the patient, that is, the estimated patient volume $VOL_{TID\_EST}$ can be obtained by the patient volume observer (virtual sensor) 33. Preferably, the estimated circuit volume $VOL_{CKT_{EST}}$ and the estimated patient volume $VOL_{TID\_EST}$ are updated according to the timing when the net flow $Q_{NET}$ crosses zero instead of the timing when the machine breaths cycles from inspiratory phase to expiratory phase. The update timing for volume variables are discussed in details as follows.

Preferably, when a patient circuit disconnect is detected or when any type of circuit integrity alarm is activated, the volume variables will not be updated until the patient circuit is reconnected or the alarm is off. That is, the measured machine delivered net volume $VOL_{NET}$, the estimated patient volume $VOL_{TID\_EST}$ and the estimated circuit volume $VOL_{CKT_{EST}}$ freeze at the previously computed values as:

$$VOL_{NET_K} = VOL_{NET_{K-1}};$$

$$VOL_{CKT_{EST_K}} = VOL_{CKT_{EST_{K-1}}}; \text{ and}$$

$$VOL_{TID_{EST_K}} = VOL_{TID_{EST_{K-1}}} \tag{11},$$

where K is an index for indicating the currently computed variables and K−1 for indicating the previously computed variables. The sampling intervals can be variable according to specific conditions, requirements, or setup parameters.

When the flow sensor 28 is installed at the patient piece 26 of the patient circuit 20, the patient flow $Q_Y$ can be measured, and a measured patient volume $VOL_{TID_Y}$ can be computed to facilitate volume limit of the pressure regulated volume delivery controller 34, so as to prevent an excessive circuit compliance pressure compensation factor $PRS_{TID_{CTL}}$ from being generated and output there from. The measured patient volume $VOL_{TID_Y}$ can also be used to replace the estimated patient volume $VOL_{TID_{EST}}$ for calculating the circuit compliance pressure compensation factor $PRS_{TID_{CTL}}$. The application of the measured patient volume $VOL_{TID_Y}$ will be discussed in details later in the specification. In addition to the measured patient volume $VOL_{TID_Y}$, another volume variable, that is, the inspiratory volume $VOL_{INSP}$ can also be obtained by integrating the inspiratory flow $Q_{INSP}$. Similarly to the volume variables presented in Equation (11), computation of these two volume variables are frozen at the previously computed values whenever the patient circuit disconnect is detected or any circuit integrity alarm is activated as:

$$VOL_{TID_{Y_K}} = VOL_{TID_{Y_{K-1}}}; \text{ and}$$

$$VOL_{INSP_K} = VOL_{INSP_{K-1}}. \tag{11-1}$$

Preferably, at the start of every inspiratory phase, or whenever any user set value of the ventilator 10 varies, the measured machine delivered net volume $VOL_{NET}$, the measured patient volume $VOL_{TID_Y}$, and the inspiratory volume $VOL_{INSP}$ are reset to an initial value (0 in this embodiment) and updated from the initial value every sampling interval (2 msec, for example) as:

$$VOL_{NET_{K-1}} = 0, \; VOL_{NET_K} = (Q_{NET_K}/60)*0.002$$

$$VOL_{TID_{Y_{K-1}}} = 0 \; VOL_{TID_{Y_K}} = (Q_{TID_{Y_K}}/60)*0.002$$

$$VOL_{INSP_{K-1}} = 0, = VOL_{INSP_K} = (Q_{INSP_K}/60)*0.002 \tag{12}$$

During the inspiratory phase, the net flow $Q_{NET}$, the patient delivered flow $Q_Y$, and the inspiratory flow $Q_{INSP}$ are continuously monitored. When the inspiratory phase has started for at least a predetermined period of time such as 50 milliseconds and the net flow $Q_{NET}$ crossed zero, that is, when $Q_{NET_K}<0$ and $Q_{NET_{K-1}}>0$, a zero-crossing net flow is detected and flagged, while the net machine delivered $VOL_{NET}$, the measured patient volumes $VOL_{TID_Y}$, and the inspiratory volume $VOL_{INSP}$ are continuously updated as:

$$VOL_{NET_K} = VOL_{NET_{K-1}} + (Q_{NET_K}/60)*0.002,$$
$$VOL_{NET_K} = \max(VOL_{NET_K}, 0)$$

$$VOL_{TID_{YK}} = VOL_{TID_{YK-1}} + (Q_{TID_{YK}}/60)*0.002,$$
$$VOL_{TID_{YK}} = \max([VOL]_1([TID_1Y]_1K), 0)$$

$$VOL_{INSP_K} = VOL_{INSP_{K-1}} + (Q_{INSP_K}/60)*0.002 \quad (13).$$

If the net flow $Q_{NET}$ has been detected to cross zero during the inspiratory phase, the estimated circuit volume $VOL_{CKT_{EST}}$ and the estimated patient volume $VOL_{TID_{EST}}$ are updated at the start of the expiratory phase following the inspiratory phase as:

$$VOL_{CKT_{ESTK}} = CKT\_CMP_{SLP} \cdot (P_{Y_K} - PEEP_K) + CKT\_CMP_{INT}$$

$$VOL_{TID_{ESTK}} = VOL_{NET_K} - VOL_{CNT_{ESTK}}$$

$$VOL_{TID_{ESTK}} = \max([VOL]_1([TID_1EST]_1K), 0) \quad (14).$$

and the machine delivered net volume $VOL_{NET}$ and the measured patient volume $VOL_{TID_Y}$ are reset to the initial setup values and updated from the initial setup values as:

$$VOL_{NET_{K-1}} = 0 \, VOL_{NET_K} = (Q_{NET_K}/60)*0.002,$$
$$VOL_{NET_K} = \min(VOL_{NET_K}, 0)$$

$$VOL_{TID_{YK}} = 0, VOL_{TID_{YK}} = (Q_{TID_{YK}}/60)*0.002,$$
$$VOL_{TID_{YK}} = \min(VOL_{TID_{YK}}, 0) \quad (15).$$

Under the condition that the net flow $Q_{NET}$ does not cross zero during the inspiratory phase, the machine delivered net volume $VOL_{NET}$ and the measured patient volume $VOL_{TID_Y}$ will not be reset at the start of the expiratory phase. That is, the machine delivered net volume $VOL_{NET}$ and the measured patient volume $VOL_{TID_Y}$ are continuously updated during the expiratory phase as Equation (13).

Following the condition that the net flow $Q_{NET}$ does not cross zero during the inspiratory phase, when the zero-crossing net flow $Q_{NET}$ is detected within a predetermined period of time such as 100 msec after the machine breath has cycled to the expiratory phase (that is, when $TIME_{EXP}<100$ msec, $Q_{NET_K}<0$ and $Q_{NET_{K-1}}>0$); or alternatively, when the expiratory phase has lasted over the predetermined period (100 msec) before the zero-crossing net flow $Q_{NET}$ is detected (that is, $TIME_{EXP}>100$ msec and $Q_{NET_K}>0$), the estimated circuit volume $VOL_{CKT_{EST}}$ and the estimated patient volume $VOL_{TID_{EST}}$ are updated according to Equation (14), while the measured machine delivered net volume $VOL_{NET}$ and the measured patient volume $VOL_{TID_Y}$ are reset and updated as:

$$VOL_{NET_{K-1}} = 0, VOL_{NET_K} = (Q_{NET_K}/60)*0.002,$$
$$VOL_{NET_K} = \min(VOL_{NET_K}, 0)$$

$$VOL_{TID_{YK}} = 0, VOL_{TID_{YK}} = (Q_{TID_K}/60)*0.002,$$
$$VOL_{TID_{YK}} = \min(VOL_{TID_{YK}}, 0) \quad (17).$$

In this embodiment, the measured machine delivered net volume $VOL_{NET}$ and the measured patient volume $VOL_{TID_Y}$ are reset according to the timing when the net flow $Q_{NET}$ crosses zero instead of the phase transition of machine breath. This allows the calculations of the estimated circuit volume $VOL_{CKT_{EST}}$ and the estimated patient volume $VOL_{TID_{EST}}$ to be synchronized with true patient inhalation and exhalation. Thereby, a more accurate patient volume can be computed. The estimated patient volume is thus updated according to the timing when the net flow $Q_{NET}$ crosses zero, such that all of the machine delivered net volume $VOL_{NET}$ can be accounted even when the patient breath and the machine breath are out of phase, that is, when the net flow $Q_{NET}$ does not cross zero at the time the machine breath is cycling to the expiratory phase.

At the beginning of every inspiratory phase, the estimated patient volume $VOL_{TID_{EST}}$ is subtracted from a set tidal volume $VOL_{TID_{SET}}$ to obtain a volume error $VOL_{TID_{ERR}}$ that reflects the error between the set tidal volume and the estimated tidal volume actually delivered to the patient. The volume error $VOL_{TID_{ERR}}$ can thus be expressed and computed from the following equation as:

$$VOL_{TID_{ERRK}} = VOL_{TID_{SETK}} - VOL_{TID_{ESTK-1}} \quad (18)$$

The volume error $VOL_{TID_{ERR}}$ or can thus be used to compute an estimated circuit compliance pressure compensation factor $PRS_{TID_{CTL}}$ by the pressure-regulated volume controller 34, so as to modulate the patient airway peak pressure $P_{SET}$ and ensure the set tidal volume delivered to the patient. At the beginning of the computation, the initial output for the regulated-pressure volume controller is input to the pressure-regulated volume controller 34, that is, the estimated circuit compliance pressure compensation factor $PRS_{TID_{CTL}}$ is initialized as:

$$PRS_{TID_{CTL}} = INI\_CKT\_PRS \quad (19).$$

The estimated circuit compliance pressure compensation factor $PRS_{TID_{CTL}}$ is reset to the initial value INI_CKT_PRS whenever the user setting of the ventilator 10 are altered. That is, any time when a new set of parameters is input to the system, the estimated circuit compliance pressure compensation factor $PRS_{TID_{CTL}}$ will be reset to the initial value INI_CKT_PRS and updated for every breath.

Figure 5:
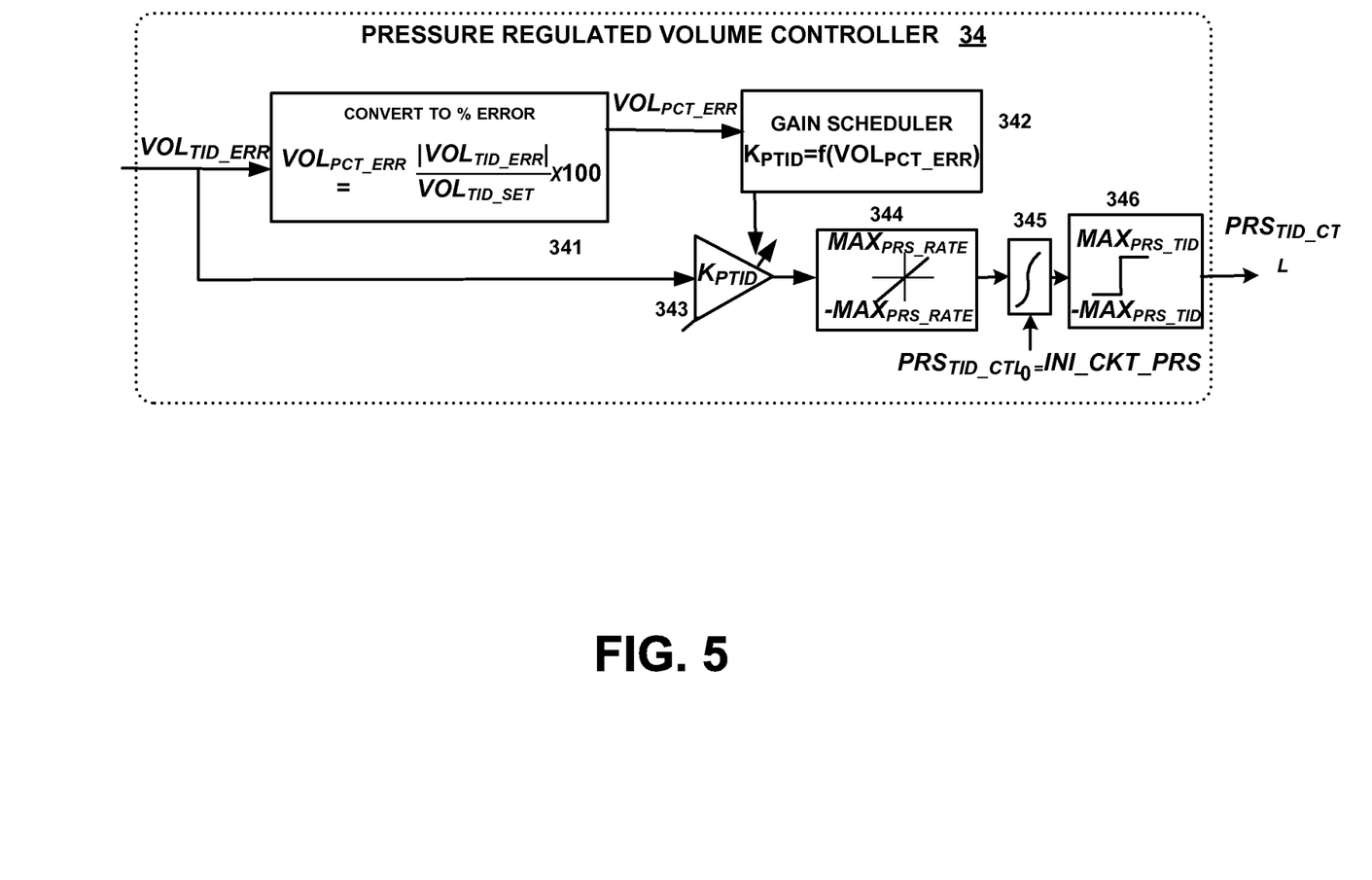
FIG. 5 illustrates a block diagram of a volume delivery controller of the system as shown in FIG. 4.

In the embodiment as shown in FIG. 5, the pressure-regulated volume controller 34 further comprises an error percentage converter 341, a gain scheduler 342, and a pressure integrator 345 for generating the circuit compliance pressure compensation volume factor $PRS_{TID_{CTL}}$ for each breath. The error percentage converter 341 is used to provide a volume error percentage defined by a ratio of an absolute value of the volume error $VOL_{TID_{ERR}}$ to the set tidal volume $VOL_{TID_{SET}}$ as $$VOL_{PCT_{ERR_K}} = \frac{|VOL_{TID_{ERR_K}}|}{VOL_{TID_{SET_K}}} \times 100. \quad (20)$$

The error percentage $VOL_{PCT_{ERR}}$ provides a useful indication of the ratio between the circuit compliance $C_T$ to the lung compliance $C_L$ of the patient. More specifically, when error percentage $VOL_{PCT_{ERR}}$ is large, it indicates that a majority of the measured delivered net volume $VOL_{NET}$ is distributed to the patient circuit 20 instead of being supplied to the patient's lung. Under such circumstance, a larger amount of volume may be required to compensate for the circuit compliance $C_T$ in order to estimate a correct machine delivered net volume which renders the volume actually delivered to the patient to the set tidal volume $VOL_{TID_{SET}}$. On the other hand, when the error percentage $VOL_{PCT_{ERR}}$ is small, it indicates the volume actually delivered to the patient is dose to the set tidal volume as desired and set up. Therefore, only a small amount of volume is required to compensate for the circuit compliance $C_T$ of the patient circuit 20. As it has been discussed above, the lung compliance $C_L$ is defined as the ratio of the volume delivered to the lung to the pressure applied to the lung of the patient ($P=V_{TID}/C_L$), the pressure is proportional to the volume delivered to the patient. Therefore, the volume error $VOL_{TID_{ERR}}$ also reflects the pressure error between the set peak airway pressure and the actually peak airway pressure applied to the patient. The pressure-regulated volume controller 34 can thus use the gain scheduler 342 to provide a gain $K_{PTID}$ according to the error percentage $VOL_{PCT_{ERR}}$. The gain $K_{PTID}$ is then input to a multiplier 343 for dynamically weighting and converting the error volume $VOL_{PCT_{ERR}}$ into a pressure weight, or namely, a pressure correction $BRTH_{PTID_{CTL}}$. Preferably, the gain $K_{PTID}$ is presented in the unit of cmH2O/ml or another other pressure unit per unit volume. With the integrator 345 as shown in FIG. 5, the circuit compliance pressure compensation factor $PRS_{TID_{CTL}}$, that is, the circuit compliance pressure compensation factor $PRS_{TID_{CTL}}$ as computed in the previous breath is updated by adding the pressure correction $BRTH_{PTID_{CTL}}$ thereto as:

$$PRS_{TID_{CTLK}} = BRTH_{PTID_{CTLK}} + PRS_{TID_{DTLK-1}} \quad (21)$$

As shown, at the beginning of the computation, that is, for the first breath when the computation starts, the value of the circuit compliance pressure compensation factor $PRS_{TID_{CTL}}$ is initialized as INI_CKT_PRS and input to the integrator 345 and continuously updated breath after breath by the pressure correction $BRTH_{PTID_{CTL}}$ obtained from the multiplier 343.

Preferably but optionally, the pressure-regulated volume controller 34 may further comprise a breath pressure correction limiter 344 and a pressure restrictor 346 to rate limit the amount of pressure correction $BRTH_{PTID_{CTL}}$ for the current breath and to prevent the updated circuit compliance pressure compensation factor $PRS_{TID_{CTL}}$ exceeding allowable ranges from being output. The allowable range for the pressure correction $BRTH_{PTID_{CTL}}$ includes a predetermined maximum value $MAX_{PRS_{RATE}}$ and a predetermined minimum value $MIN_{PRS_{RATE}}$. In this embodiment, a symmetric upper and lower limit is selected for the allowable range of the pressure correction $BRTH_{PTID_{CTL}}$. That is, the minimum value $MIN_{PRS_{RATE}}$ is set as the negative maximum value as $-MAX_{PRS_{RATE}}$, such that the pressure correction $BRTH_{PTID_{CTL}}$ output from the breath pressure correction limiter 344 will be limited as:

$$BRTH_{PTID_{CTLK}} = \max(K_{PTID} * VOL_{TID_{ERRK}} - MAX_{PRS_{RATE}})$$

$$BRTH_{PTID_{CTLK}} = \min(BRTH_{PTID_{CTLK}}, MAX_{PRS_{RATE}}) \quad (22)$$

Figure 6:
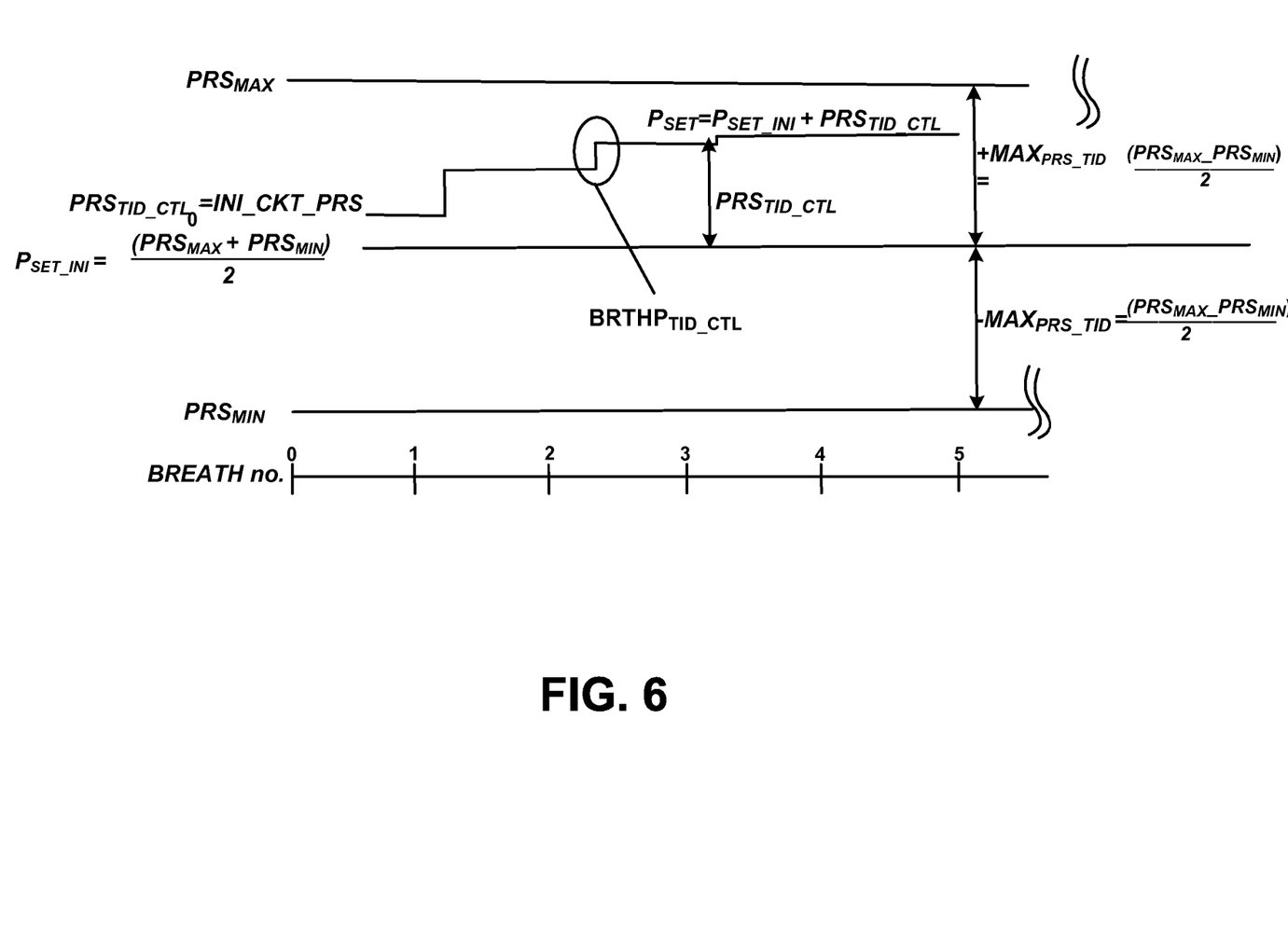
FIG. 6 illustrates the regulated peak airway pressure for a plurality of breaths.

Referring in FIGS. 4 and 6, the circuit compliance compensated pressure-regulated volume control system 30 further comprises an initial target pressure calculator 35 to calculate the initial peak airway pressure $P_{SET_{INI}}$ defined as an average of a predetermined maximum value $PRS_{MAX}$ and a predetermined minimum value $PRS_{MIN}$ for the target peak airway pressure $P_{SET}$ as:

$$P_{SET_{INI}} = (PRS_{MAX} + PRS_{MIN})/2 \quad (23)$$

As shown, the initial value of the circuit compliance pressure compensation factor $PRS_{TID_{CTL}}$ is preset as INI_CKT_PRS, and the updated circuit compliance pressure compensation factor $PRS_{TID_{CTL}}$ is limited between $MAX_{PRS_{TID}}$ and $-MAX_{PRS_{TID}}$ by the pressure restrictor 346 as:

$$PRS_{TID_{CTL}} = \min(MAX_{PRS_{TID}}, PRS_{TID_{CTL}})$$

$$PRS_{TID_{CTL}} = \max(-MAX_{PRS_{TID}}, PRS_{TID_{CTL}})$$

$$MAX_{PRS_{TID}} = (PRS_{MAX} - PRS_{MIN})/2 \quad (24).$$

Thereby, the target peak airway pressure $P_{SET}$ can also be limited between $PRS_{MAX}$ and $PRS_{MIN}$ to avoid excessive adjustment that will cause adverse or harmful effect to the patient.

As discussed above, the measured patient volume $VOL_{TID_Y}$ can be used as a volume limit reference to prevent the pressure-regulated volume controller 34 from excessively generating the circuit compliance pressure compensation factor $PRS_{TID_{CTL}}$. To this extent, the system for circuit compliance compensated pressure control 30 further comprises a volume limiter 37 to receive the measured patient volume $VOL_{TID_Y}$ and compare the measured patient $VOL_{TID_Y}$ to the set tidal volume $VOL_{TID_{SET}}$. Before the measured patient volume $VOL_{TID_Y}$ reaches the set tidal volume $VOL_{TID_{SET}}$, that is, when $VOL_{TID_Y} < VOL_{TID_{SET}}$, the pressure regulated volume controller 34 operates normally to generate the circuit compliance pressure compensation factor $PRS_{TID_{CTL}}$ according to Equation (21). Once the measured patient volume $VOL_{TID_Y}$ reaches the set tidal volume $VOL_{TID_{SET}}$, the circuit compliance pressure compensation factor $PRS_{TID_{CTL}}$ is frozen at the value computed in the previous breath as:

$$PRS_{TID_{CTLK}} = PRS_{TID_{CTLK-1}} \quad (25).$$

Effectively, the volume limiter 37 is operative to switch on or activate operation of the pressure regulated volume controller 34 when the measured patient volume $VOL_{TID_Y}$ is smaller than the set tidal volume $VOL_{TID_{SET}}$, and switch off or inactivate operation of the pressure-regulated volume controller 34 when the measured patient volume $VOL_{TID_Y}$ is equal to or larger than the set tidal volume $VOL_{TID_{SET}}$. It will be appreciated that when the actual measured patient volume $VOL_{TID_Y}$ is used for feedback, a volume limiter 37 will not be needed since the volume error $VOL_{TID_{ERR}}$ would be 0 when actual measured patient volume $VOL_{TID_Y}$ reaches the set tidal volume $VOL_{TID_{SET}}$; and consequently, the circuit compliance pressure compensation factor $PRS_{TID_{CTL}}$ updated by the weighted volume error $VOL_{TID_{CTL}}$ will remain the same as that computed in the previous breath expressed as Equation (25).

Referring to FIG. 4, the circuit compliance pressure compensation factor $PRS_{TID_{CTL}}$ generated and output by the pressure-regulated volume controller 34 is then input to an adder/subtractor 303, in which the peak airway pressure $P_{SET_{INI}}$ is input and added to the circuit compliance pressure compensation factor $PRS_{TID_{CTL}}$ as:

$$P_{SET_K} = PRS_{TID_{CTLK}} + P_{SET_{INIK}} \quad (26),$$

where $P_{SET_{INI}} = (PRS_{MAX} + PRS_{MIN})/2$ in this embodiment.

The estimated peak airway pressure $P_{SET}$ is then input to the ventilator 10 and patient circuit 20 via the servo control subsystem 40, such that the ventilator 10 can provide a circuit compliance compensated peak airway pressure $P_{SET}$ applied to the patient, so as to ensure the ventilator 10 delivering sufficient volume which allows the set tidal volume $VOL_{TID_{SET}}$ delivered to the patient as desired. As shown in FIG. 4, the servo control subsystem 40, upon receiving the updated peak airway pressure $P_{SET}$, is operative to output a flow control signal $FCV_{D/A}$ to the ventilator 10 for controlling the flow control valve at the inspiratory port 14. Thereby, the inspiratory flow $Q_{INSP}$ output from the inspiratory port 14 can be adjusted to provide the updated peak airway pressure $P_{SET}$. The servo control subsystem 40 is further operative to output an exhalation valve control $EV_{D/A}$ to control the open/close timing or status of the expiratory port 16 of the ventilator 10 in order to control exhalation of the patient.

Further referring to FIG. 4, in the pressure control mode, the machine breath is controlled to cycle from an inspiratory phase to an expiratory phase preset at $T_{INSP_{SET}}$. Therefore, when the inspiratory phase reaches the preset phase transition time $T_{INSP_{SET}}$, the machine breath is cycling from the inspiratory phase to the expiratory phase, and depending on the timing when the net flow $Q_{NET}$ crosses zero, the estimated circuit volume $VOL_{CKT_{EST}}$ and the estimated patient volume $VOL_{TID_{EST}}$ are updated. The transition of phase is detected by a phase detector 36 as shown in FIG. 4, for example.

Further referring to FIG. 4, the system of circuit compliance compensated pressure control 30 further comprises a plurality of adders/subtractors 301, 302, and 303. As shown, the adder/subtractor 301 is operative to receive the inspiratory flow $Q_{INSP}$ and the expiratory flow $Q_{EXP}$, so as to calculate and provide the measured machine delivered net volume $VOL_{NET}$ to the patient volume observer 32. The adder/subtractor 302 has two inputs to receive the set tidal volume $VOL_{TID_{SET}}$ and the estimated patient volume $VOL_{TID_{EST}}$ from the patient volume observer 32. Thereby, the volume error $VOL_{TID_{ERR}}$ between the set tidal volume $VOL_{TID_{SET}}$ and the estimated patient volume $VOL_{TID_{EST}}$, that is, the error between the desired tidal volume and actual tidal volume delivered to the patient can be estimated. The adder/subtractor 303 adds the circuit compliance pressure compensation factor $PRS_{TID_{CTL}}$ to the set peak airway pressure $P_{SET_{INI}}$ to obtain a target peak airway pressure $P_{SET}$. The output of the adder/subtractor 303 is connected to the servo control subsystem 40, from which the ventilator 10 is informed with the target peak airway pressure $P_{SET}$ to be supplied to the patient. The circuit compliance compensated pressure regulated volume control system 30 further includes integrators 312 and 313 to compute the measured machine delivered volume $VOL_{NET}$ and the measured patient volume $VOL_{TID_Y}$ when the Y circuit flow $Q_Y$ is measured, respectively.

As discussed above, the measured patient volume $VOL_{TID_Y}$ can be used to as a volume limit reference in a volume limiter 37 for controlling operation of the pressure-regulated volume controller 34. Preferably, the volume limit is reset at the beginning of every inspiratory phase and cleared whenever the Y flow sensor is not in use. In certain circumstances, the measured patient volume $VOL_{TID_Y}$ can be used to replace the estimated patient volume $VOL_{TID_{EST}}$ for computing the circuit compliance pressure compensation factor $PRS_{TID_{CTL}}$. Such application can be implemented by installing a switch 38 which selectively connects the output of integrator 313 or the patient volume observer 33 to the pressure-regulated volume controller 34 via the adder 302.

The above adders/subtractors, 301-303 and integrators 312-313 may be individually formed individually in the system 30; or alternatively, they can also be integrated into the respective devices. For example, the integrators 312 may be integrated into the patient volume observer 33 and the adder/subtractors 301 and 302 may be integrated as a portion of the patient volume observer 33 and the pressure-regulated volume delivery controller 34, respectively. The adder/subtractor 303 may also be integrated at the output of the pressure-regulated volume delivery controller 34. In addition, the circuit compliance compensated pressure-regulated volume control system 30 may be implemented by individual hardware or a processor integrated into the ventilator 10. The circuit compliance compensated pressure-regulated volume control system 30 may also be implemented by a software executable by a personal or laptop computer connected to the ventilator or by the processor of the ventilator 10 directly.

The above description is given by way of example, and not limitation. Given the above disclosure, one skilled in the art could devise variations that are within the scope and spirit of the invention disclosed herein, including various ways of implementing the circuit compliance compensated volume control systems. Further, the various features of the embodiments disclosed herein can be used alone, or in varying combinations with each other and are not intended to be limited to the specific combination described herein. Thus, the scope of the claims is not to be limited by the illustrated embodiments.

What is claimed is:

1. A ventilation system, comprising:
   a ventilator operatively having an inspiratory port for supplying an inspiratory gas to a patient and an expiratory port for receiving an expiratory gas from a patient;
   a patient circuit having an inspiratory limb having one end connected to the inspiratory port, an expiratory limb having one end connected to the expiratory port, and a patient piece having one end connected to the other ends of the inspiratory and expiratory limbs and the other end connected to the patient; and
   a circuit compliance compensated pressure regulated volume control system, comprising a pressure-regulated volume controller operative to generate a circuit compliance pressure compensation factor based on a volume error defined as a volume differential between a set tidal volume and a volume actually delivered to the patient.

2. The ventilation system of claim 1, further comprising a device for integrating a patient flow $Q_Y$ measured at the patient piece of the patient circuit into a measured patient volume reflecting the volume actually delivered to the patient.

3. The ventilation system of claim 1, further comprising a patient volume observer for providing an estimated patient volume reflecting the volume actually delivered to the patient, wherein the estimated patient volume is obtained based on a measured machine delivered net volume and a circuit compliance of the patient circuit.

4. The ventilation system of claim 3, further comprising a circuit compliance estimator for estimating the circuit compliance as a relationship between a circuit volume and a circuit pressure.

5. The ventilation system of claim 4, further comprising a circuit volume estimator for providing a circuit volume based on the relationship estimated by the circuit compliance estimator.

6. The ventilation system of claim 5, wherein the patient volume observer is operative to provide the estimated patient volume by subtracting the circuit volume from the measured machine delivered net volume.

7. The ventilation system of claim 1, wherein the pressure-regulated volume controller comprises: an error percentage converter for providing a volume error percentage as a ratio of an absolute value of the volume error to the set tidal volume;
   a gain scheduler operative to provide a gain $K_{PTID}$ for converting the volume error into an estimated pressure correction; and
   a pressure integrator for updating the circuit compliance pressure compensation factor by adding the estimated pressure correction thereto, wherein the circuit compliance pressure compensation factor is initialized into a preset initial value at a first breath when computation thereof is started and updated breath after breath.

8. The ventilation system of claim 7, wherein the pressure-regulated volume controller further comprising a multiplier for multiplying the gain with the volume error to obtain the estimated pressure correction.

9. The ventilation system of claim 7, wherein the circuit compliance pressure compensation factor is reset to the initial value when any user preset parameter is changed.

10. The ventilator system of claim 1, further comprising an adder for updating a peak airway pressure by adding the circuit compliance pressure compensation factor thereto.

11. The ventilation system of claim 10, further comprising a servo control subsystem for controlling the inspiratory and expiratory ports according to the updated peak airway pressure.

\* \* \* \* \*